(12) United States Patent
Hall et al.

(10) Patent No.: US 11,585,734 B2
(45) Date of Patent: Feb. 21, 2023

(54) TOILET WITH INFRASTRUCTURE FOR ANALYTICAL DEVICES

(71) Applicant: Hall Labs, LLC, Provo, UT (US)

(72) Inventors: David R. Hall, Provo, UT (US); David Crismon, Herriman, UT (US); Joshua Larsen, Provo, UT (US); Jared Reynolds, Provo, UT (US); Kevin Jeffrey Campbell, Provo, UT (US)

(73) Assignee: Medic, Inc., Provo, UT (US)

( * ) Notice: Subject to any disclaimer, the term of this patent is extended or adjusted under 35 U.S.C. 154(b) by 0 days.

(21) Appl. No.: 16/811,918

(22) Filed: Mar. 6, 2020

(65) Prior Publication Data

US 2020/0393337 A1 Dec. 17, 2020

Related U.S. Application Data

(60) Provisional application No. 62/981,470, filed on Feb. 25, 2020, provisional application No. 62/979,803, (Continued)

(51) Int. Cl.
*B01L 3/00* (2006.01)
*E03D 11/13* (2006.01)
(Continued)

(52) U.S. Cl.
CPC ....... *G01N 1/2035* (2013.01); *A61B 5/02055* (2013.01); *A61B 5/6891* (2013.01); *A61B 10/0038* (2013.01); *B01L 3/5027* (2013.01); *B01L 3/50273* (2013.01); *B01L 3/502715* (2013.01); *B01L 3/502738* (2013.01); *E03D 11/13* (2013.01); *G01N 1/18* (2013.01); *G01N 1/38* (2013.01); *G01N 21/255* (2013.01); *G01N 33/4833* (2013.01); *G01N 33/493* (2013.01); *A61B 5/021* (2013.01); *A61B 5/0245* (2013.01); *A61B 5/02444* (2013.01); *A61B 5/14542* (2013.01); *A61B 5/208* (2013.01);
(Continued)

(58) Field of Classification Search
CPC .... E03D 11/00; E03D 11/13; B01L 3/502715; B01L 3/5027; B01L 3/50273; B01L 3/502; B01L 3/50; B01L 2300/023; B01L 2300/025; B01L 2300/047; B01L 2300/0627; B01L 3/502738; A61B 5/02055; A61B 5/6891; A61B 5/318; A61B 5/021; A61B 5/14542
USPC ............... 4/3, 300; 422/50, 502, 501, 500
See application file for complete search history.

(56) References Cited

U.S. PATENT DOCUMENTS

2009/0216099 A1* 8/2009 Kim ................. A61B 5/022
600/345
2010/0061889 A1* 3/2010 Park ................. G01N 33/493
422/400

(Continued)

OTHER PUBLICATIONS

Merriam-Webster, Receptacle Definition, obtained from https://www.merriam-webster.com/dictionary/receptacle on Apr. 21, 2022. (Year: 2022).*

*Primary Examiner* — Christine T Mui

(57) ABSTRACT

An analytical toilet comprising a bowl for receiving excreta from a user; a base supporting the bowl; a supply of flush water; and a plurality of receptacles, each providing mechanical attachment, a power supply, and a data connection to an analytical device, which analytical device is adapted to provide data useful to the user is disclosed.

21 Claims, 12 Drawing Sheets

Related U.S. Application Data filed on Feb. 21, 2020, provisional application No. 62/912,429, filed on Oct. 8, 2019, provisional application No. 62/888,972, filed on Aug. 19, 2019, provisional application No. 62/888,700, filed on Aug. 19, 2019, provisional application No. 62/862,610, filed on Jun. 17, 2019.

(51) Int. Cl.
| | |
|---|---|
| *G01N 1/20* | (2006.01) |
| *G01N 21/25* | (2006.01) |
| *G01N 33/493* | (2006.01) |
| *G01N 33/483* | (2006.01) |
| *G01N 1/18* | (2006.01) |
| *A61B 10/00* | (2006.01) |
| *A61B 5/0205* | (2006.01) |
| *A61B 5/00* | (2006.01) |
| *G01N 1/38* | (2006.01) |
| *A61B 5/021* | (2006.01) |
| *A61B 5/145* | (2006.01) |
| *A61B 5/20* | (2006.01) |
| *A61B 5/024* | (2006.01) |
| *A61B 5/0245* | (2006.01) |
| *A61B 5/318* | (2021.01) |
| *E03D 9/08* | (2006.01) |
| *G01N 33/48* | (2006.01) |
| *E03D 11/00* | (2006.01) |

(52) U.S. Cl.
CPC ............. *A61B 5/318* (2021.01); *A61B 10/007* (2013.01); *A61B 10/0012* (2013.01); *A61B 2562/0247* (2013.01); *A61B 2562/0257* (2013.01); *A61B 2562/0271* (2013.01); *B01L 2200/10* (2013.01); *B01L 2200/16* (2013.01); *B01L 2300/023* (2013.01); *B01L 2300/025* (2013.01); *B01L 2300/047* (2013.01); *B01L 2300/0627* (2013.01); *B01L 2300/0819* (2013.01); *B01L 2400/0415* (2013.01); *B01L 2400/0605* (2013.01); *E03D 9/08* (2013.01); *E03D 11/00* (2013.01); *G01N 33/48* (2013.01); *G01N 2001/205* (2013.01)

(56) References Cited

U.S. PATENT DOCUMENTS

2017/0322197 A1* 11/2017 Hall ................. G01N 33/493
2018/0165417 A1*  6/2018 Hall ........................ A47K 4/00

* cited by examiner

TOILET WITH INFRASTRUCTURE FOR ANALYTICAL DEVICES

CROSS-REFERENCE TO RELATED APPLICATIONS

This application claims priority to U.S. Provisional Patent Application No. 62/862,610 titled "Toilet Providing Infrastructure for Multiple Health Analysis Tools" filed on Jun. 17, 2019; 62/888,700 titled "Plug and Play Platform for Analyzing Biological Samples" filed on Jun. 17, 2019; 62/888,972 titled "Toilet with Digitally Controlled Manifold to Distribute Water, Air and Excreta" filed on Aug. 28, 2019; 62/912,429 titled "Toilet with Microfluidic Chips for Testing Samples" filed on Oct. 8, 2019; 62/979,803 titled "Analytical Toilet for Assessing Analytes in Excreta" filed Feb. 21, 2020; and 62/981,470 titled "Analytical Toilet for Assessing Analytes in Excreta" filed on Feb. 25, 2020, which are incorporated herein by reference in their entireties.

TECHNICAL FIELD

The present disclosure relates to analytical toilets. More particularly, it relates to analytical toilets equipped to provide health information to the user.

BACKGROUND

The ability to track an individual's health and wellness is currently limited to the lack of available data related to personal health. Many diagnostic tools are based on examination and testing of excreta, but the high cost of frequent doctor's visits and/or scans make these options available only on a very limited and infrequent basis. Thus, they are not widely available to people interested in tracking their own personal wellbeing.

Toilets present a fertile environment for locating a variety of useful sensors to detect, analyze, and track trends for multiple health conditions. Locating sensors in such a location allows for passive observation and tracking on a regular basis of daily visits without the necessity of visiting a medical clinic for collection of samples and data. Monitoring trends over time of health conditions supports continual wellness monitoring and maintenance rather than waiting for symptoms to appear and become severe enough to motivate a person to seek care. At that point, preventative care may be eliminated as an option leaving only more intrusive and potentially less effective curative treatments. An ounce of prevention is worth a pound of cure.

Smart toilets have been developed that provide health and wellness data for a user by analyzing various properties of samples of excreta by multiple sensors. Adding new or updated sensors to a medical device can be difficult if the geometry or connection scheme are incompatible with a previous interface.

Microfluidics offer the benefits of testing samples using smaller volumes and reduced costs associated with reduced material usage and reduced pumping needs. However, microfluidics also requires a support structure to deliver and extract samples that is very precisely designed, manufactured, and fitted.

Just a few examples of smart toilets and other bathroom devices can be seen in the following U.S. patents and Published applications: U.S. Pat. No. 9,867,513, entitled "Medical Toilet With User Authentication"; U.S. Pat. No. 10,123,784, entitled "In Situ Specimen Collection Receptacle in a Toilet and Being in Communication with a Spectral Analyzer"; U.S. Pat. No. 10,273,674, entitled "Toilet Bowl for Separating Fecal Matter and Urine for Collection And Analysis"; US 2016/0000378, entitled "Human Health Property Monitoring System"; US 2018/0020984, entitled "Method of Monitoring Health While Using a Toilet"; US 2018/0055488, entitled "Toilet Volatile Organic Compound Analysis System for Urine"; US 2018/0078191, entitled "Medical Toilet for Collecting and Analyzing Multiple Metrics"; US 2018/0140284, entitled "Medical Toilet with User Customized Health Metric Validation System"; US 2018/0165417, entitled "Bathroom Telemedicine Station." The disclosures of all these patents and applications are incorporated by reference in their entireties.

SUMMARY

In a first aspect, the disclosure provides an analytical toilet comprising a bowl for receiving excreta from a user; a base supporting the bowl; a supply of flush water; and a plurality of receptacles, each providing mechanical attachment, a power supply, and a data connection to an analytical device, which analytical device is adapted to provide data useful to the user.

Further aspects and embodiments are provided in the foregoing drawings, detailed description and claims.

BRIEF DESCRIPTION OF THE DRAWINGS

The following drawings are provided to illustrate certain embodiments described herein. The drawings are merely illustrative and are not intended to limit the scope of claimed inventions and are not intended to show every potential feature or embodiment of the claimed inventions. The drawings are not necessarily drawn to scale; in some instances, certain elements of the drawing may be enlarged with respect to other elements of the drawing for purposes of illustration.

DETAILED DESCRIPTION

Figure 1:
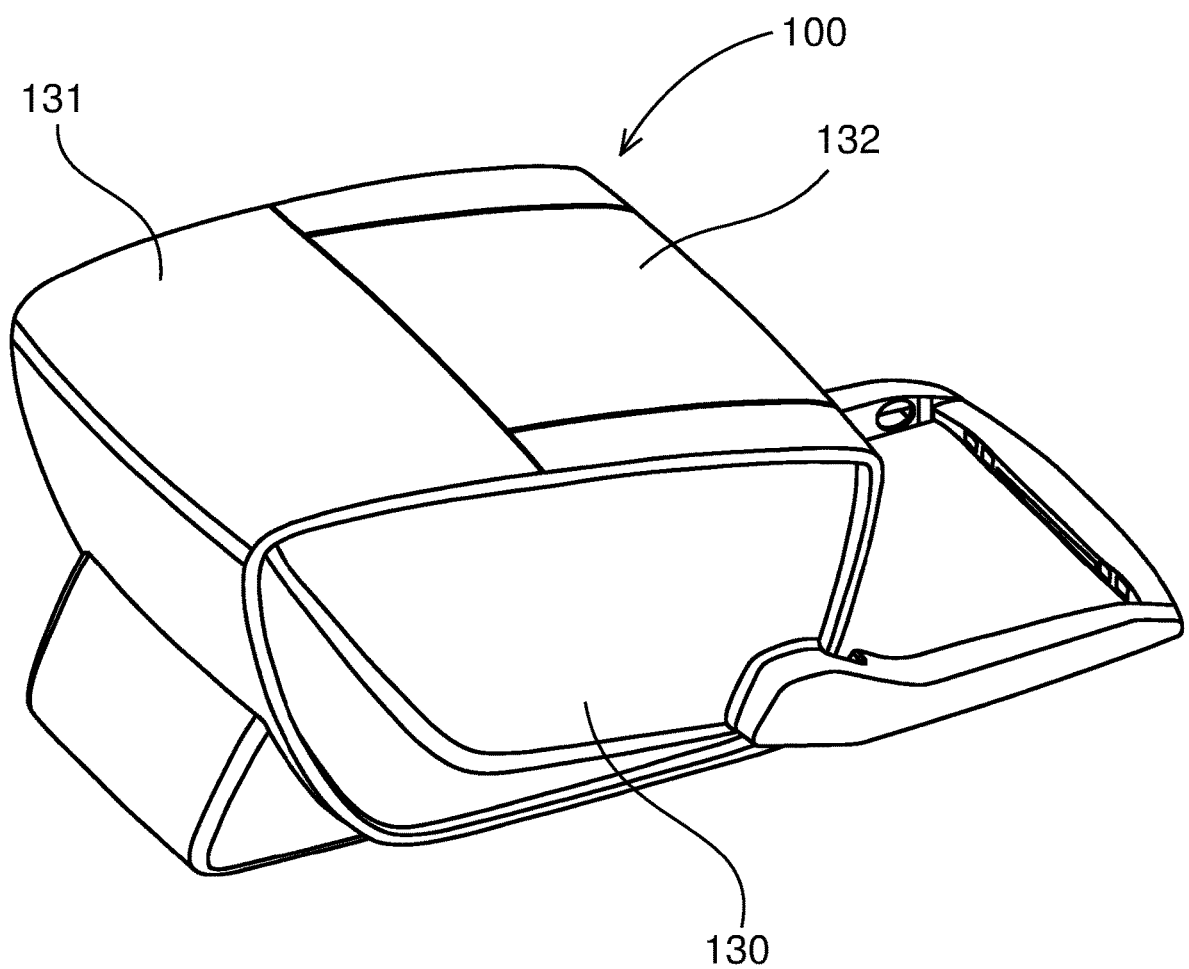
FIG. 1 is a perspective view of a first exemplary embodiment of an analytical toilet according to the present disclosure.

The following description recites various aspects and embodiments of the inventions disclosed herein. No particular embodiment is intended to define the scope of the invention. Rather, the embodiments provide non-limiting examples of various compositions, and methods that are included within the scope of the claimed inventions. The description is to be read from the perspective of one of ordinary skill in the art. Therefore, information that is well known to the ordinarily skilled artisan is not necessarily included.

Definitions

The following terms and phrases have the meanings indicated below, unless otherwise provided herein. This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure and are not meant to be limiting in any fashion. Nor do these phrases indicate any kind of preference for the disclosed embodiment.

As used herein, "toilet" is meant to refer to any device or system for receiving excreta, including urinals.

As used herein, the term "bowl" refers to the portion of a toilet that is designed to receive excreta.

As used herein, the term "base" refers to the portion of the toilet below and around the bowl supporting it.

As used herein, the term "user" refers to any individual who interacts with the toilet and deposits excreta therein.

As used herein, the term "excreta" refers to any substance released from the body of a user including urine, feces, menstrual discharge, and anything contained or excreted therewith.

As used herein, the term "manifold" is intended to have a relatively broad meaning, referring to a device with multiple conduits and valves to controllably distribute fluids, namely water, liquid sample and air.

As used herein, the term "test chamber" is meant to refer broadly to any space adapted to receive a sample for testing, receive any other substances used in a test, and apparatus for conducting a test, including any flow channel for a fluid being tested or used for testing.

As used herein, the term "sensor" is meant to refer to any device for detecting and/or measuring a property of a person or substance regardless of how that property is detected or measured, including the absence of a target molecule or characteristic.

As used herein, a "fluidic circuit" is meant to refer to the purposeful control of the flow of a fluid. Often, this is accomplished through physical structures that direct the fluid flow. Sometimes, a fluidic circuit does not include moving parts.

As used herein, a "fluidic chip" is meant to refer to a physical device that houses a fluidic circuit. Often, a fluidic chip facilitates the fluid connection of the fluidic circuit to a body of fluid.

As used herein, the term "microfluidics" is meant to refer to the manipulation of fluids that are contained to small scale, typically sub-millimeter channels. The "micro" used with this term and others in describing this invention is not intended to set a maximum or a minimum size for the channels or volumes.

As used herein, the term "microfluidic chip" is meant to refer to is a set of channels, typically less than 1 $mm^2$, that are etched, machined, 3D printed, or molded into a microchip. The micro-channels are used to manipulate microfluidic flows into, within, and out of the microfluidic chip. A microfluidic chip may include features or channels that are not micro-sized in addition to at least one component, function, or feature that is micro-sized.

As used herein, the term "microfluidic chamber" is meant to refer to a test chamber adapted to receive microfluidic flows and/or a test chamber on a microfluidic chip.

As used herein, the term "lab-on-chip" is meant to refer to a device that integrates one or more laboratory functions or tests on a single integrated fluidic circuit. Lab-on-a-chip devices are a subset of microelectromechanical systems (MEMS) and are sometimes called "micro total analysis systems" ($\mu$TAS).

As used herein, the term "data connection" and similar terms are meant to refer to any wired or wireless means of transmitting analog or digital data and a data connection may refer to a connection within a toilet system or with devices outside the toilet.

Exemplary Embodiments

The present disclosure relates to analytical toilets (may also be referred to as an "analytical toilet" or a "health and wellness" toilet) with analytical tools to perform scientific tests on excreta samples to identify potential health and wellness indicators. More particularly, it relates to the use of modular testing devices with standardized mechanical connection and interfaces providing, as appropriate for particular tests, electrical power, data connection, fluid inlets, and fluid outlets.

In accordance with the present disclosure, an analytical toilet that includes an infrastructure for multiple health and wellness analysis tools is provided. This provides a platform for the development of new analytical tools by interested scientists and companies. Newly developed tests and diagnostic tools may be readily adapted for use in a system having a consistent tool interface.

In various exemplary embodiments, the analytical toilet provides a fluid processing manifold that collects and routes samples from the toilet bowl to various scientific test devices and waste handling portals throughout the device. In a preferred embodiment, the manifold is digitally controlled. A digitally controlled manifold may include analog component or circuits.

In various exemplary embodiments, the medical toilet provides multiple fluid sources via a manifold system. The manifold is adapted to connect to a plurality of analytic test devices adapted to receive fluids from the manifold. The manifold is designed to selectively provide a variety of different fluid flows to the analytical test device. These fluids may include, among others, excreta samples, buffer solutions, reagents, water, cleaners, biomarkers, dilution solutions, calibration solutions, and air. These fluids may be provided at different pressures and temperatures. The manifold and analytical test device are also adapted to include a fluid drain from the analytical test devices.

In various exemplary embodiments, the manifold system provides a standardized interface for analytical test devices to connect and receive all common supplies (e.g., excreta samples, flush water), data, and power. Common supplies may be supplied from within (e.g., reagents, cleaners) or without (e.g., water) the toilet system. The analytical test devices may be designed to receive some or all of the standardized flows. The analytical test devices may also include storage cells for their own unique supplies (e.g., test reagent).

In various exemplary embodiments, the manifold is adapted to direct fluids from one or more sources to one or more analytical test devices. The manifold and analytical test devices are designed such that analytical test devices can be attached to and detached from the manifold making them interchangeable based on the needs of the user. Different analytical test devices are designed to utilize different test methods and to test excreta samples for different constituents.

In various exemplary embodiment, the smart toilet provides an electrical power connection and a data connection for the analytical test device. In a preferred embodiment, the electrical power and data connections use the same circuit. In various exemplary embodiments, the toilet is provided with pneumatic and/or hydraulic power to accommodate the analytical test devices.

In various exemplary embodiments, the smart toilet platform performs various functions necessary to prepare samples for examination. These functions include, but are not limited to, liquidizing fecal samples, diluting or concentrating samples, large particle filtration, sample agitation, and adding reagents. Miniaturized mechanical emulsification chambers show promise for repeatable and sanitary stool preparation. Stool samples may also be liquefied using acoustic energy and/or pressurized water jets.

In various exemplary embodiments, the smart toilet also provides, among other things, fluid transport, precise fluid metering, fluid valving, fluid mixing, separation, amplification, storage and release, heating of fluid, cooling of fluid, and incubation. The smart toilet also is equipped to provide cleansers, sanitizers, rinsing, and flushing of all parts of the system to prevent cross-contamination of samples. In some embodiments, the system produces electrolyzed water for cleaning.

In various exemplary embodiments, one layer of the fluidic manifold is dedicated to macro-scale mixing of fluids. Sample, diluents, and reagents are available as inputs to the mixers. The mixing chamber is placed in series with all other scientific test devices, allowing bulk mixed sample to be routed to anywhere from one to all stations (i.e., analytical test device interfaces) for analysis. Mixing may also occur in an analytical test device.

In various exemplary embodiments, samples are filtered for large particulates at the fluid ingress ports of the manifold. The fluid manifold uses a network of horizontal and vertical channels along with simple valves to route prepared stool samples to one of several scientific test devices located on the platform.

In various exemplary embodiments, samples are filtered for particulates larger than a particular threshold, defined appropriately for the application. In some embodiments, multiple filters may be used sequentially or be available in parallel. One layer of the manifold stack may be dedicated as an interchangeable filter module, or a more monolithic purpose-build manifold may be the design of choice. The fluid manifold uses a network of horizontal and vertical channels along with simple valves to route filtered urine or stool samples to one of several scientific test devices located on the platform. The filter mechanism is placed in series with all other scientific test devices, allowing filtered sample to be routed to anywhere from one to all stations (i.e., analytical test device interfaces) for analysis. Filtering may also occur in an analytical test device.

In various exemplary embodiments, the manifold is constructed using additive layers, and different layers can be customized for particular applications. Standard ports and layouts are used for interfacing with external components, such as pressure sources and flow sensors. In general, characteristic channel volumes at the first layers of the manifold stack are on the order of milliliters. At the final level of the manifold stack is the microfluidic science device, which will interface simultaneously with multiple microfluidic chips using standardized layout and pressure seals.

In various exemplary embodiments, the analytic test devices are designed to perform one or more of a variety of laboratory tests in a toilet environment. Any test that could be performed in a medical or laboratory setting may be implemented in an analytical test device in a toilet. These tests may include measuring pulse, blood pressure, blood oxygenation, electrocardiography, body temperature, body weight, excreta content, excreta weight, excreta volume, excreta temperature, excreta density, excreta flow rate, and other health and wellness indicators.

In various exemplary embodiments, the system is adapted to work with a variety of actuation technologies that may be used in the analytical test devices. The system provides electronic and fluidic interconnects for various actuator technologies and supports OEM equipment. In a preferred embodiment, the system is adapted to work with actuator modules that can be attached to the sample delivery manifold and controlled by a central processor. The system platform supports an inlet and outlet for the pressure transducer that interfaces with the fluidic manifold, and electronic or pneumatic connections where required. The system supports a variety of macro- and microfluidic actuation technologies including, but not limited to, pneumatic driven, mechanical pumps (e.g., peristaltic, diaphragm), on-chip check-valve actuators (e.g., piezo-driven or magnetic), electroosmotic driven flow, vacuum pumps, and capillary or gravity driven flow (i.e., with open channels and vents).

One benefit of the present disclosure is the detection, monitoring, and tracking of a user's biomarkers without having any inconvenience aside from what they would otherwise do using the toilet. Without the present disclosure, among other things, people often have to manually collect samples of solid excreta, use equipment they are less familiar with than a toilet, or wait longer for analysis and results. Each of these things can negatively impact a user's experience and/or the quality or accuracy of the results.

Figure 2:
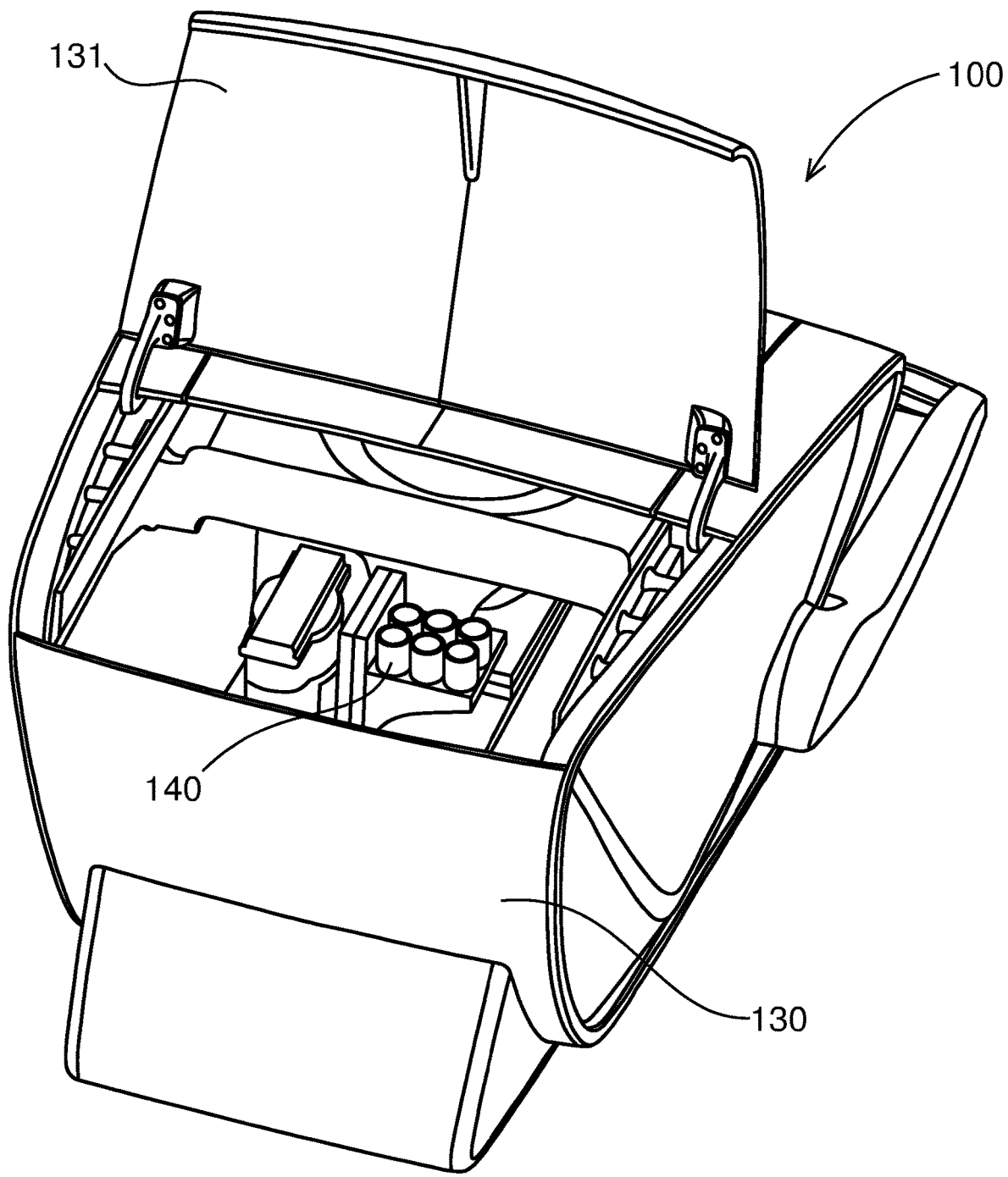
FIG. 2 is a rear perspective view of the toilet of FIG. 1 with the rear compartment open.
Figure 3:
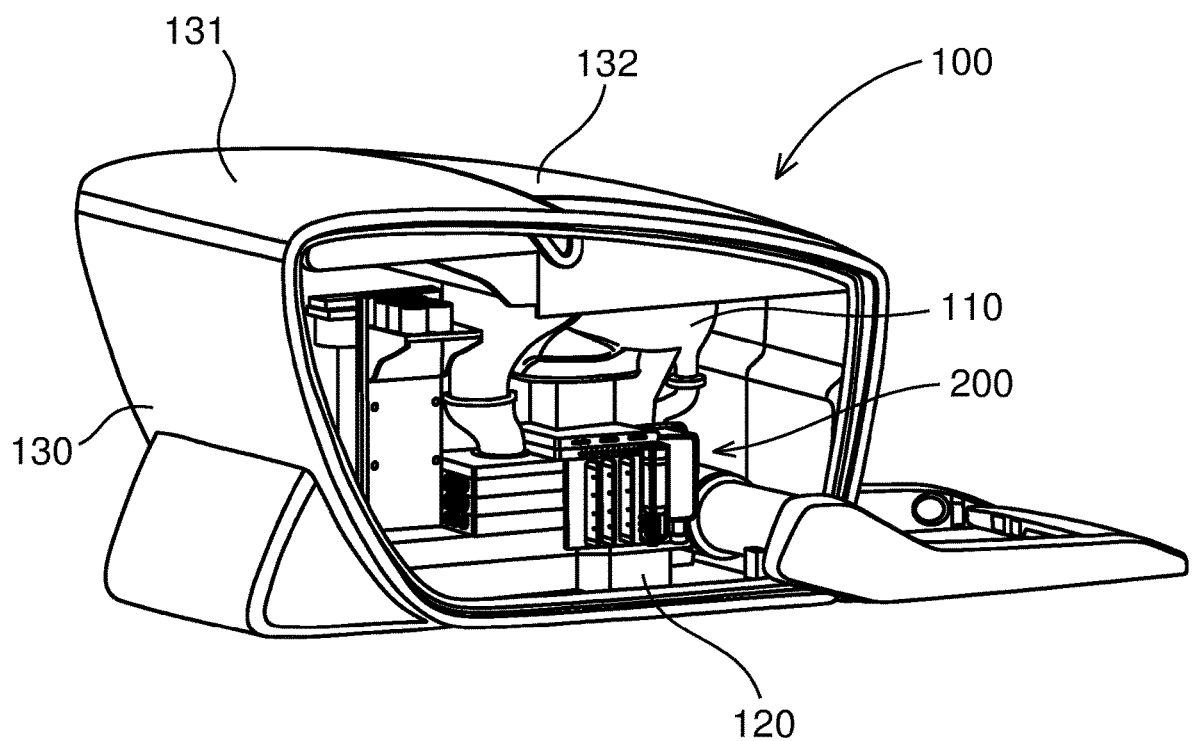
FIG. 3 is a side perspective view of the toilet of FIG. 1 with a side panel removed to show the interior of the toilet.

Now referring to FIGS. 1-3, a first embodiment of an analytical toilet 100 is shown. FIG. 1 shows the toilet seat, bowl, plumbing, and other internal components covered by a shroud 130 that includes a rear cover 131 and lid 132. FIG. 2 shows the toilet with a rear cover 131 of the shroud 130 open showing part of the interior of the toilet. In this embodiment, this portion of the toilet 100 includes fluid containers 140 that hold supplies used for some of the functions of the analytical toilet 100 (e.g., analytical tests, cleaning, disinfecting, sample preparation, etc.). FIG. 3 shows the toilet 100 with a side panel of the shroud 130 removed to allow showing the interior components of the toilet 100, including the bowl 110, base 120, and manifold 200.

Figure 4:
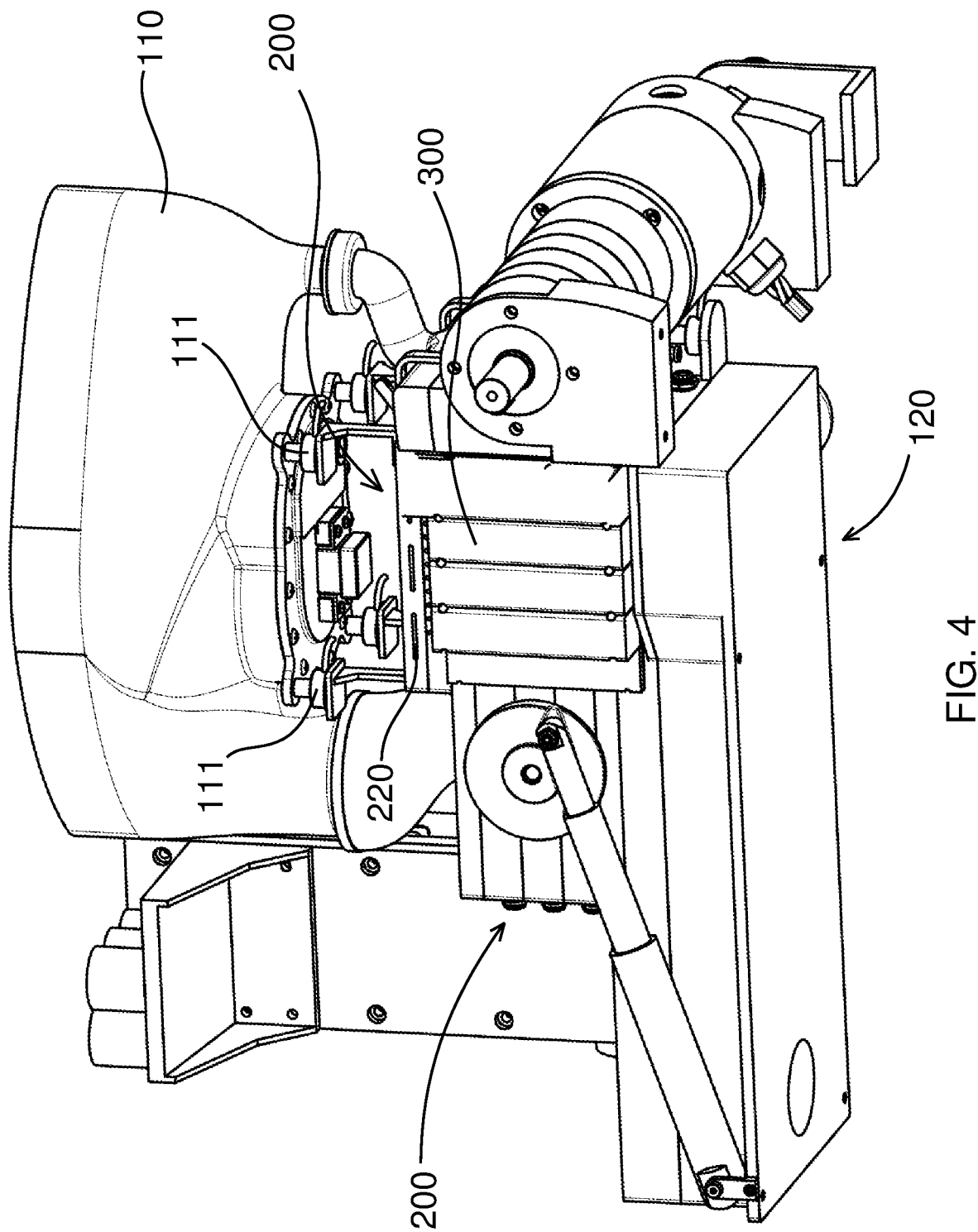
FIG. 4 is a side perspective view of the manifold of the toilet of FIG. 1.

Now referring to FIG. 4, the interior of the toilet of FIGS. 1-3 is shown. The internal components of the toilet 100 are supported by a base 120. The bowl 110 is supported by one or more load cells 111. A manifold 200 is located below the bowl 110. The manifold 200 comprises a plurality of fluid paths. These fluid paths allow the manifold 200 to move fluids between the bowl 110, fluid containers 140, outside sources (e.g., municipal water supplies), other sources (e.g., air or water electrolyzing unit), analytical test devices 300, and the toilet outlet. The manifold 200 also provides electrical power and data connections to the analytical test devices 300. The manifold 200 can also directly pass fluids and/or solids from the bowl 110 to the toilet outlet. The manifold 200 provides multiple fluidic circuits including transport channels, valves, and pumps.

Figure 5:
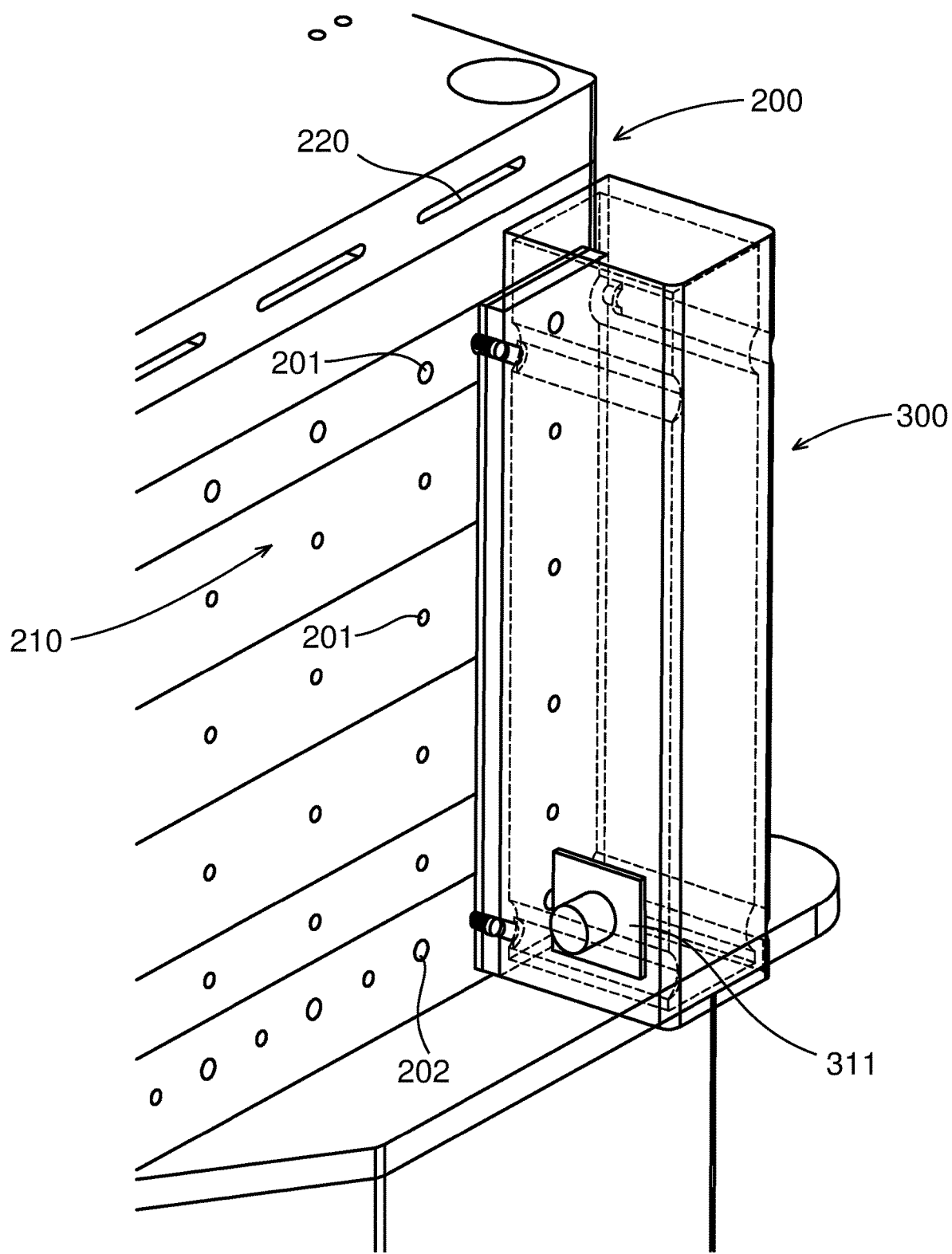
FIG. 5 is a perspective view of a first exemplary embodiment of an analytical test device attached to a medical toilet according to the present disclosure.

Now referring to FIG. 5, a first embodiment of a modular analytical test device 300 attached to an exemplary embodiment of a manifold 200 is shown. The manifold 200 is adapted to provide receptacles 210 with standardized connection interfaces for multiple analytical test devices 300. The manifold 200 is shown here with multiple fluid sources 201 for the analytical test device 300. In various embodiments, the manifold 200 may include receptacles 210 for more than one type of analytical test device 300 (e.g., different sizes, fluid supply needs, etc.).

In various exemplary embodiment, the analytical test device 300 includes multiple inlets in fluid communication with the manifold 200. The selected fluid flows are directed into a test chamber with one or more sensors 311 (flow channels internal to the analytical test device not shown in FIG. 5). The sensors 311 may be one or more of electrochemical sensors, spectrometers, chromatography, charge-coupled device (CCD), or metal oxide semiconductor field-effect transistor (MOSFET) including complementary metal oxide semiconductor field-effect transistor (CMOSFET). The analytic test device 300 also includes at least one outlet 302 or drain 202 in fluid communication with the manifold 200.

Figure 6:
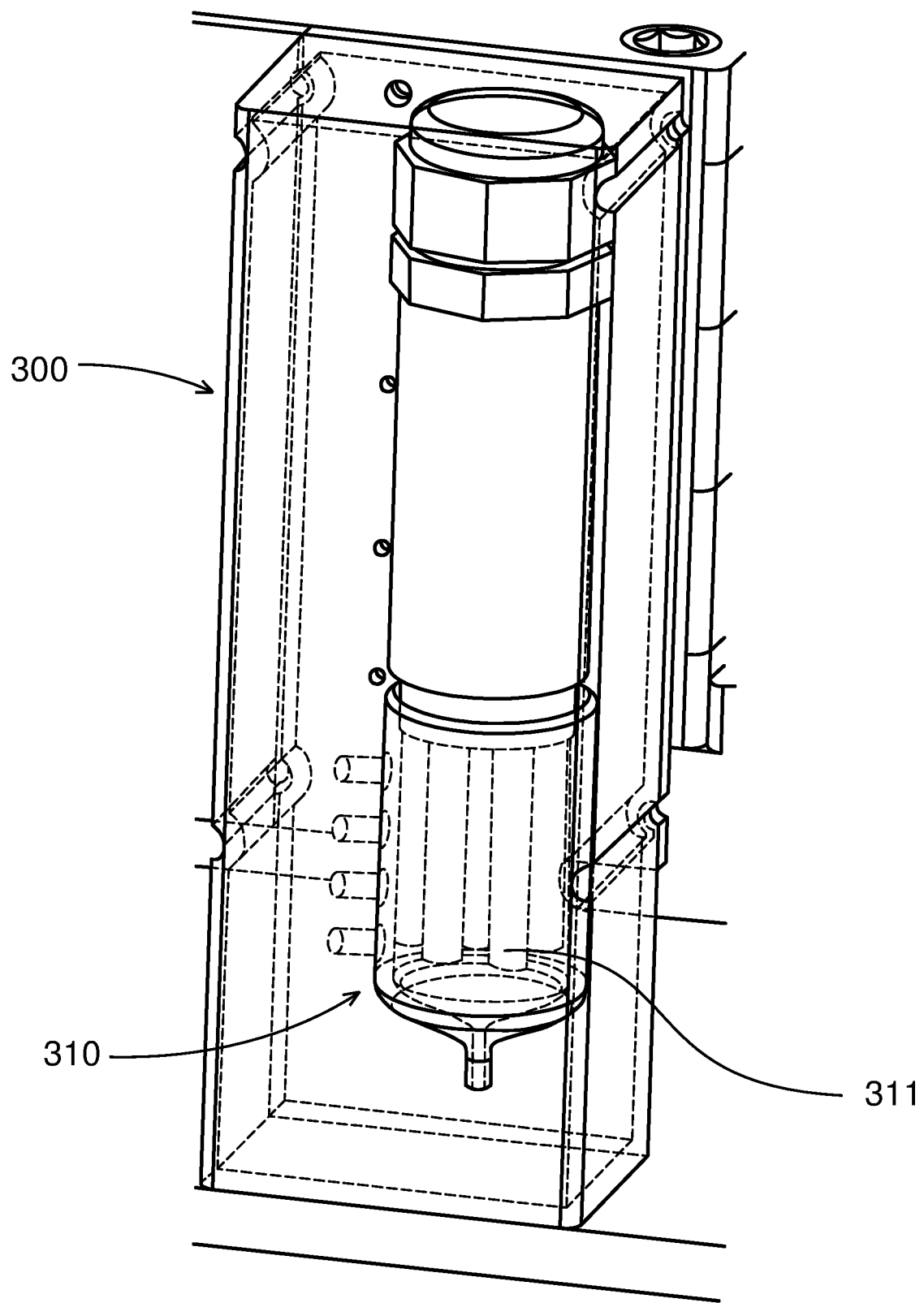
FIG. 6 is a perspective view of a second embodiment of an analytical test device according to the present disclosure.

Now referring to FIG. 6, a second embodiment of a modular analytical test device 300 is shown. The analytical test device 300 includes multiple fluid inlets 301, test chamber 310, and at least one fluid outlet 302. The analytic test device 300 includes a test chamber 310 that received fluid flows and contains at least one array of sensors 311.

Figure 7:
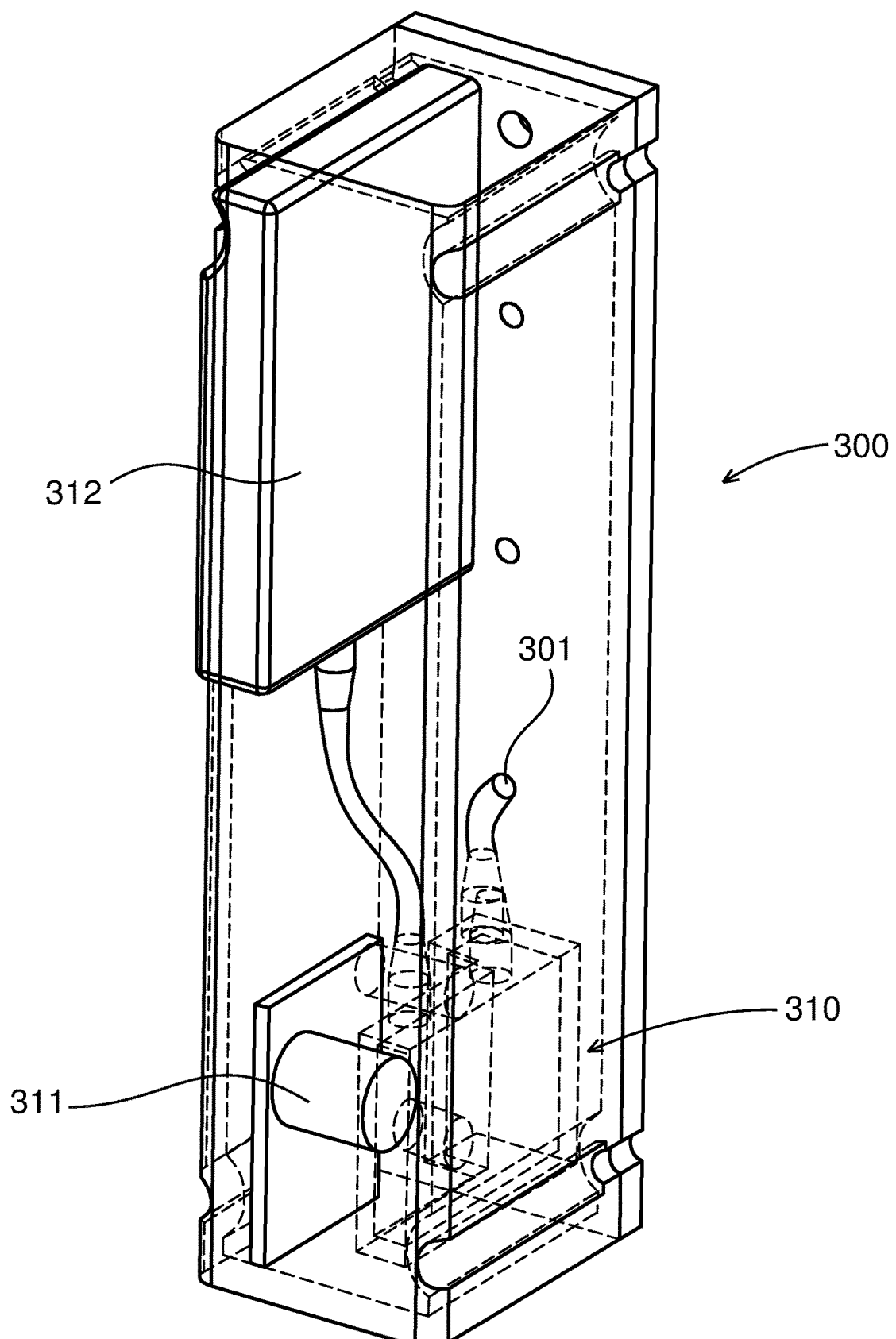
FIG. 7 is a perspective view of a third embodiment of a health and wellness analytical test device according to the present disclosure.

Now referring to FIG. 7, a third embodiment of a modular analytical test device 300 is shown. The analytical test device 300 includes multiple fluid inlets 301, test chamber 310, and at least one fluid outlet 302. This embodiment of an analytical test device 300 includes a storage cell 312, also in fluid communication with the test chamber 310. The analytical test device 300 may also include a pump to move fluid (e.g., test reagent) from the cell 312 to the test chamber 310. The analytic test device 300 also includes a camera adjacent to the test chamber 310 to monitor the contents of the test chamber 310. In various embodiments, the test chamber 310 is used to mix an excreta sample with a reagent that will cause a color change if a target analyte is present in the excreta sample. The camera is adapted to detect the color change. In various exemplary embodiments, the camera may be used to observe other characteristics or changes to the sample in the test chamber 310 (e.g., urine settling).

In various exemplary embodiments, the analytic test device 300 includes one or more ports for a microfluidic chip ("MFC"). The microfluidic interfaces 220 are designed to receive a MFC and provide it with all necessary power, data, and fluidic connections. Microfluidics are used to transport samples and other fluids to and from the MFC. In a preferred embodiment, the MFC includes a test chamber with a lab-on-chip ("LoC") (also known as test-on-chip). The LoC may be designed to perform one or more laboratory tests. The fluidic circuits and sensors may be as small as micro or nano sized.

Figure 8:
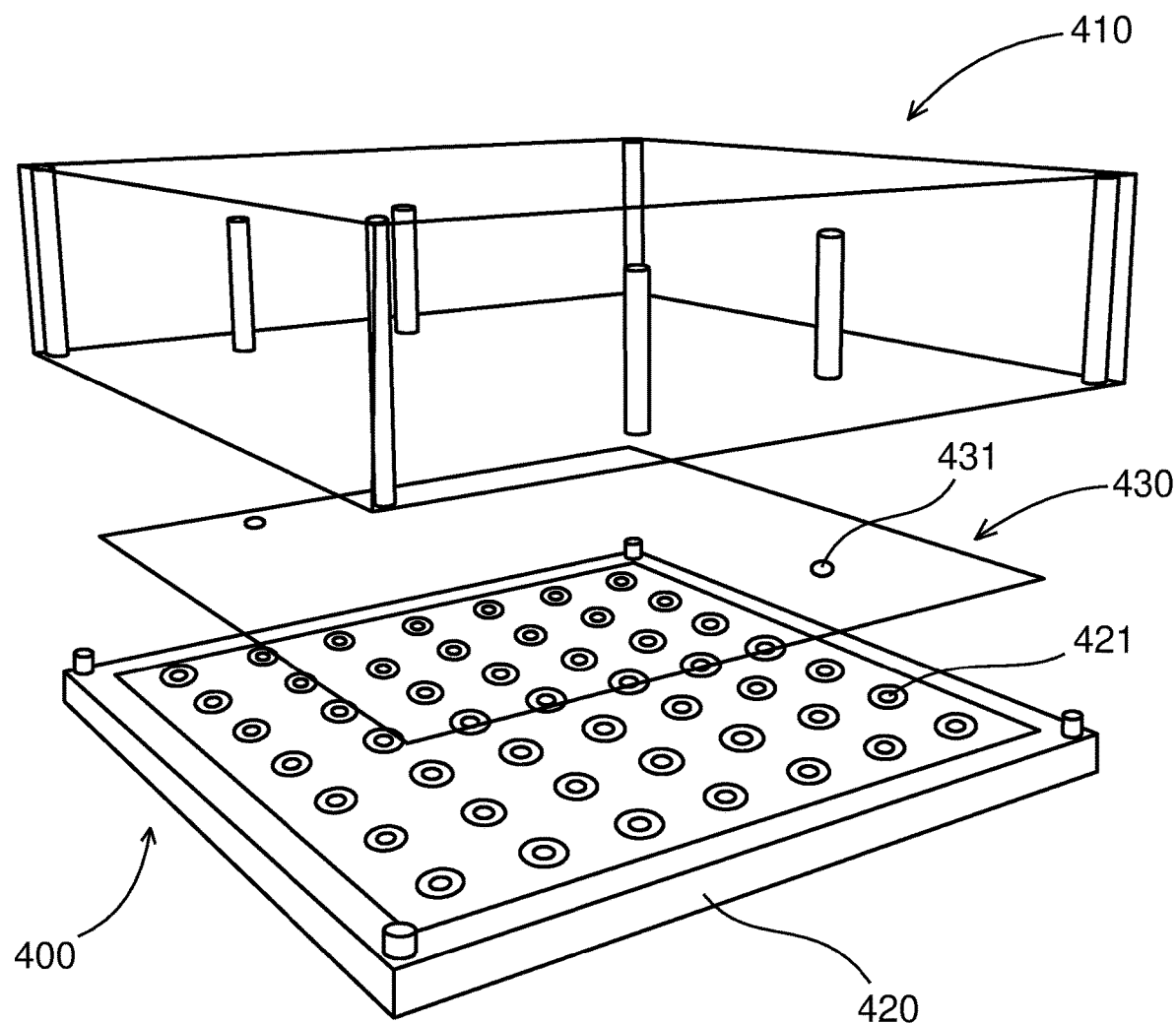
FIG. 8 is an exploded perspective view of an exemplary embodiment of a microfluidic lab on chip fluid interface.

Now referring to FIG. 8, an exemplary embodiment of an analytical test device 300 adapted for use with a microfluidic chip ("MFC") is shown. The MFC analytic test device 400 includes a test chamber 410 with a lab on chip 411. The manifold 200 includes a plurality of slots 220 or other openings for placement of a MFC analytical test device 400. An interface 420 with multiple ports 421, which act as fluid inlets or outlets for the test chamber 410, to provide connections and/or supplies for the MFC analytic test device 400. Protrusions 422 encircle the ports 421 to provide a point of positive contact for the sealing gasket 430, minimizing dead volume. Pores 431 in the gasket 430 select or block possible interactions with the MFC analytic test device 400.

In various exemplary embodiments, the backplate interface 420 is machined or molded with multiple microfluidic pores 421 for ingress of fluids or for removal of fluids. The interface 420 can be used with a variety of MFC analytic test device 400 testing modules. The ports 421 are preferably sealed by placing a gasket 430 between the MFC analytic test device 400 and backplate 420. The gasket 430 may be designed with pores 431 to selectively allow fluid flow through selected ports 421 and block potential flow through others depending on the MFC analytic test device 400 design. The gasket 430 may have alignment holes or features, with matching structures in the interface 420 or MFC analytic test device 400, to facilitate aligning the sheet of material to the pores 431. For example, the gasket 430 may fit snugly in a recess in the interface 420, or alignment pins in the interface 420 may match holes patterned in the gasket 430 by the same process used to create the pores 431. The gasket 430 may have corrugations, or variations in thickness, or be composed of multiple layers of different materials designed to reduce distortions propagating from one point of contact to another, in order to improve the alignment of the gasket 430 to the pores 431 during installation or when the system is pressurized.

In various exemplary embodiments, the gasket 430 may function as a seal for otherwise open channels in the MFC analytic test device 400, permitting pressurized flow in those channels. The gasket 430, typically an electrical insulator, may have electrical contacts built into the top, bottom, or intermediate layers of material, or embedded within the gasket 430 material. The gasket 430 may have electrical contacts built to cause a voltage potential to exist in the fluid. The gasket 430 may have electrical contacts built on the surface to come into contact with the fluid or gas and provide a potential to create electrochemical interactions. The gasket 430 may have electrical contacts built on the surface to come into contact with the fluid or gas and measure the electrical potential or ionic current.

In various exemplary embodiments, when the MFC analytic test device 400 is mechanically clamped to the plate 420 with sufficient pressure, the gasket 230 material creates a high-pressure seal between the MFC analytic test device 400 and the interface 420. Pores 431 in the gasket 430 open a channel between the backplate 420 and the MFC analytic test device 400. The gasket 430 material may be optimized for the application, including selecting chemically inert material. Alternatively, each pore 431 may be circumscribed with an elastomer O-ring that provides a seal under pressure.

Figure 9:
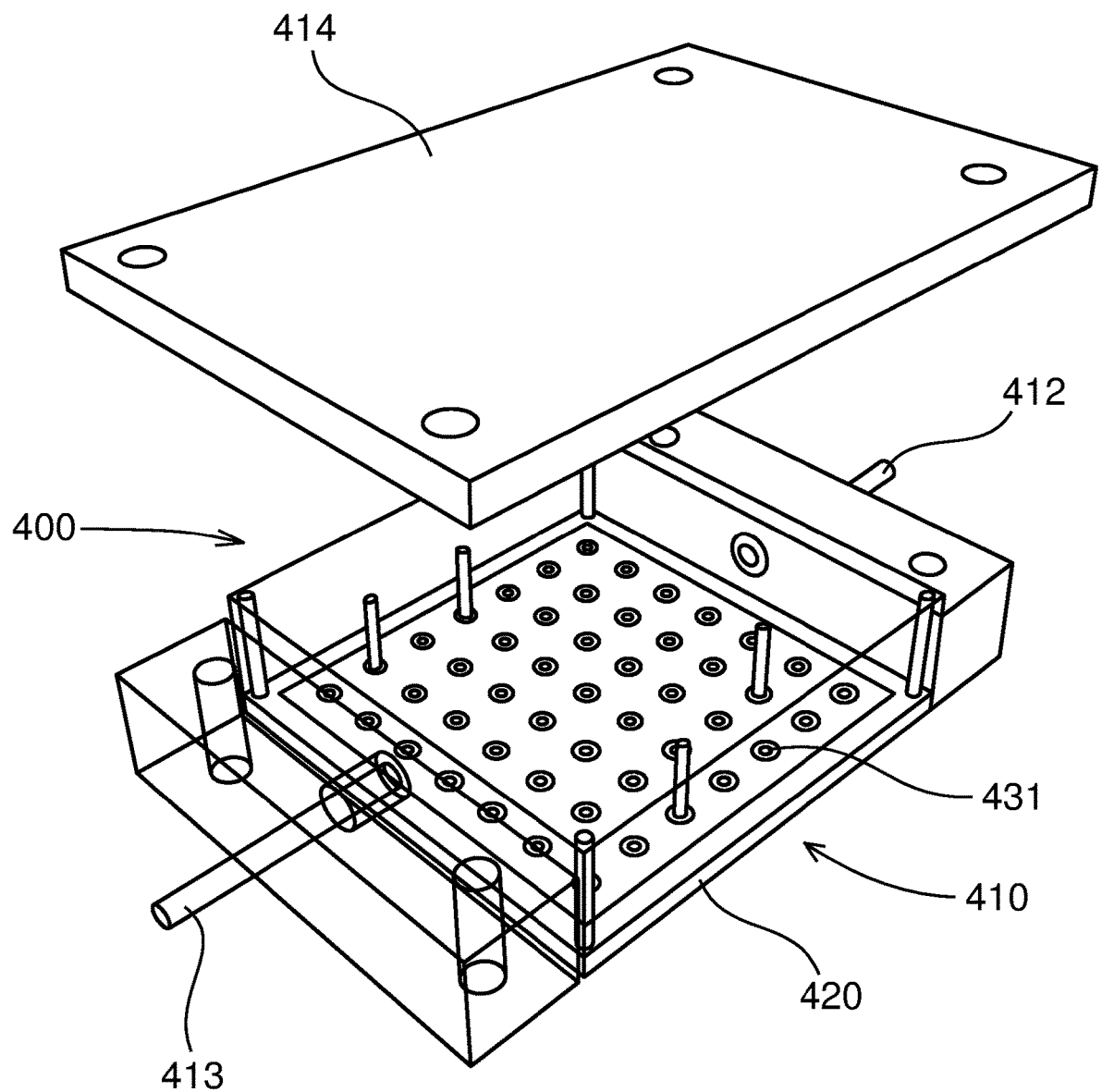
FIG. 9 is an exploded perspective view of an exemplary embodiment of an optical interface for a microfluidic system, in lateral configuration.

Now referring to FIG. 9, an exemplary embodiment of an MFC analytic test device 400 with an optical interface is shown. In some embodiments, a light source and light detector are connected to the test chamber 410 by fiber optic cables 412 and 413 are part of the test chamber 410 (e.g., spectrometer). The MFC analytic test device 400 is attached to the interface and held in place by a clamp plate. In an alternative embodiment, the light source 412 may be placed in the clamp plate 414 to deliver light to a standardized location normal to the MFC analytic test device 400.

In various exemplary embodiments, the light detector may include various mechanisms for reducing reflections, such as covering the detector with an anti-reflection coating, film. The light detector may be an optical waveguide or other photonic sink.

In various exemplary embodiments, the MFC analytic test device 400 is secured to the interface 420 by a clamp 414 In a preferred embodiment, the clamp 414 serves a dual purpose as a back-side interface for microfluidic ports 421 in the reverse side of the MFC analytic test device 400. Microchannels machined into the clamp 414 in standardized locations may be included in the clamp design.

In various exemplary embodiments, the microfluidic fixtures, including screw-in connectors, may interface with micro-tubing to provide a connection elsewhere in the system, or back to the same chip. The micro-tubing may provide chip-to-chip connections.

In various exemplary embodiments, the clamp may serve as a housing or mounting point for a mirror that directs laser light through the MFC analytic test device 400. Some implementations may use a semi-transparent mirror that allows several MFC analytic test devices 400 arranged in a line to use the same laser beam to interact with MFC analytic test device 400 components. The platform microfluidic interface/manifold provides ports intended for this purpose.

Figure 10:
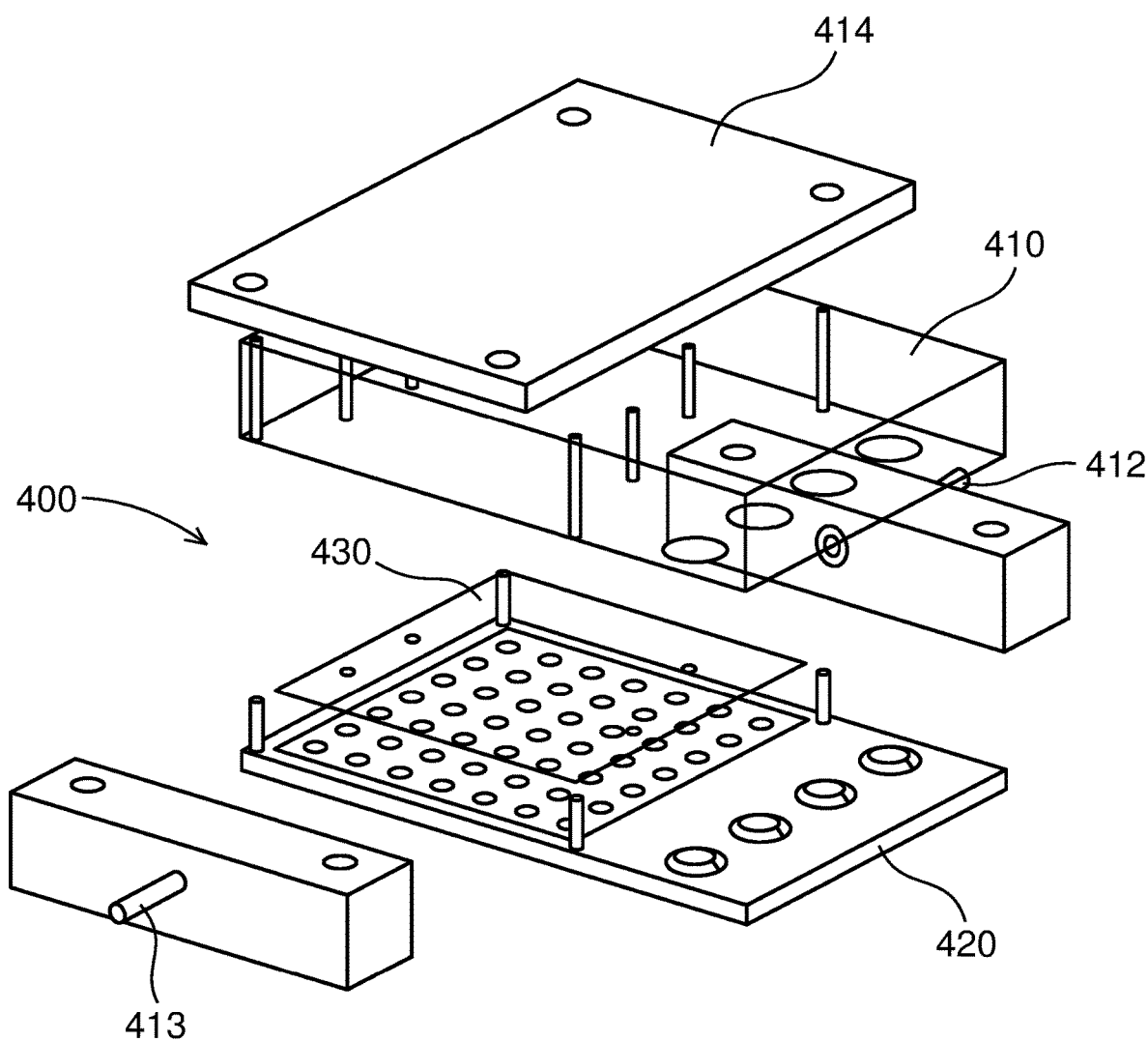
FIG. 10 is an exploded perspective view of an exemplary embodiment of an interface including of a set of electrical contacts.

Now referring to FIG. 10, an exemplary embodiment of an MFC analytic test device 400 with a set of electrical contacts is shown. Electrical pads in a standardized location are made available for generic electrical operations, such as providing high and low voltage contacts, control signals, and ground pins. Corresponding pads are also located on the MFC analytic test device 400.

Figure 11:
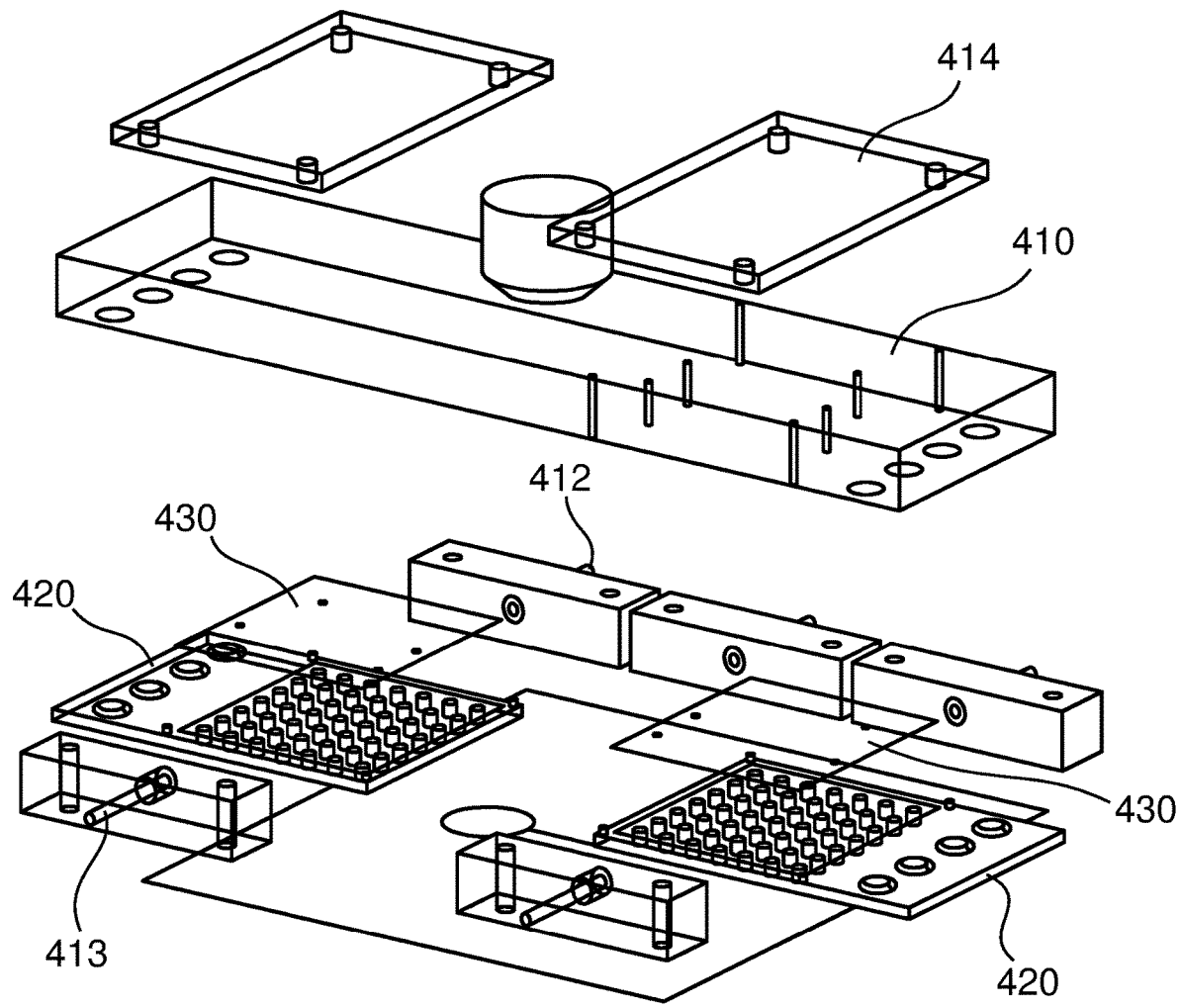
FIG. 11 is an exploded perspective view of an exemplary embodiment of an alternate configuration for a larger chip with additional standardized areas designated for fluidic, electrical or optical interconnects.

Now referring to FIG. 11, an alternate configuration is shown for a larger MFC analytic test device 400 with additional standardized areas designated for fluidic, electrical, or optical interconnects. This embodiment shows a designated viewing area, where a light source illuminates the MFC analytic test device 400 from below, and an image detector (possibly including a microscope or other magnifier) examines the output. Other embodiments may include an electronically controlled shutter that selectively blocks the light or selects a pinhole/orifice size for the light. The light source may be visible, UV, or other wavelength range of light emissions. The light source may be wide-band or narrow band.

In various exemplary embodiments, the MFC analytical test device 400 is designed to use very small quantities of reagent. In various exemplary embodiments, reagents are dispensed using technology similar to that used in inkjet printers to dispense ink. In some embodiments, an electrical current is applied piezoelectric crystal causing its shape or size to change forcing a droplet of reagent to be ejected through a nozzle. In some embodiments, an electrical current is applied to a heating element (i.e., resistor) causing reagent to be heated into a tiny gas bubble increasing pressure in the reagent vessel forcing a droplet of reagent to be ejected.

In various exemplary embodiments, the toilet fluidic manifold provides routing. Interconnecting levels of channels allows routing from one port to all others. Each channel may include a pressure dampener to facilitate constant pressure pumping of all active channels simultaneously, while time-multiplexing pump-driven inflow. Fluids may be supplied by the manifold in continuous or segmented flow (e.g., separated by air bubbles). The sensors may collect data continuously during exposure or may take discrete data points. Once the testing parameters are reached and reliable data is collected that is within a pre-determined range, the data may then be statistically evaluated. The mean, median, and standard deviation of the data may be carried out. Additionally, regression analysis may be carried out on the data of a single user. Regression analysis may also be used on two or more users to understand how the data of a single user compares to a population of users of the analytical toilet.

In various exemplary embodiments, the manifold has reaction chambers built in for general purpose mixing operations. Each chamber has a macro-sized channel through which the manifold delivers a urine sample (filling the reaction chamber), and the chamber has a micro-sized channel. Pumps located internal or external to the manifold drive fluid into the reaction chamber, and into the micro-sized channel. A valve at the output of the macro-channel, and possibly at the output of the micro-channel, controls fluid direction as it exits the reaction chamber.

Microfluidic applications require support infrastructure for sample preparation, sample delivery, consumable storage, consumable delivery or replenishment, and waste extraction. In various exemplary embodiments, the manifold includes integrated support for differential pressure applications, pneumatic operations, sample and additive reservoirs, sample accumulators, external pumps, pneumatic pressure sources, active pump pressure (e.g., peristaltic, check-valve actuators, electro-osmotic, electrophoretic), acoustic or vibrational energy, and light-interaction (e.g., spectrometer, colorimeter, laser, UV, magnification).

In various exemplary embodiments, the sensor to detect a particular analyte is integrated into a planar substrate with the active portion of the sensor exposed. Example substrates may be glass, plastic, ceramic, metal, etc. The planar sensor may be affixed to the manifold as described for the semiconductor embodiment.

In various exemplary embodiments, the manifold interface has a matrix of ports, possibly laid out in a regular grid. These ports may be activated or closed via an external support manifold. Routing is fully programmable.

In various exemplary embodiments, the manifold directs one or more fluids to the analytical test device 300 or MFC analytical test device 400 to cleanse the devices. These may include cleaning solutions, disinfectants, and flushing fluids. In various exemplary embodiments, the manifold directs hot water or steam to clean sample, reagents, etc. from the devices. In various exemplary embodiments, the toilet systems using oxygenated water, ozonated water, electrolyzed water, which may be generated on an as-needed basis by the toilet system (this may be internal or external to the toilet).

In various exemplary embodiments, waste from the MFCs is managed based on its characteristics and associated legal requirements. Waste that can be safely disposed is discharged into the sewer line. Waste that can be rendered chemically inert (e.g., heat treatment, vaporization, neutralization) is processed and discharged. Waste that cannot be discharged or treated in the toilet system is stored, and sequestered if necessary, for removal and appropriate handling.

In various exemplary embodiments, the manifold creates sequestered zones for each of these waste categories and ensures that all products are properly handled. In various exemplary embodiments, the manifold directs flushing water and/or cleansing fluids to clean the manifold and MFC. In some embodiments, high-pressure fluids are used for cleaning. In such an embodiment, the high-pressure fluids are not used in the MFC. In some embodiments, the MFC is removed from the backplate interface and all ports are part of the high-pressure cleansing and/or rinse.

Figure 12:
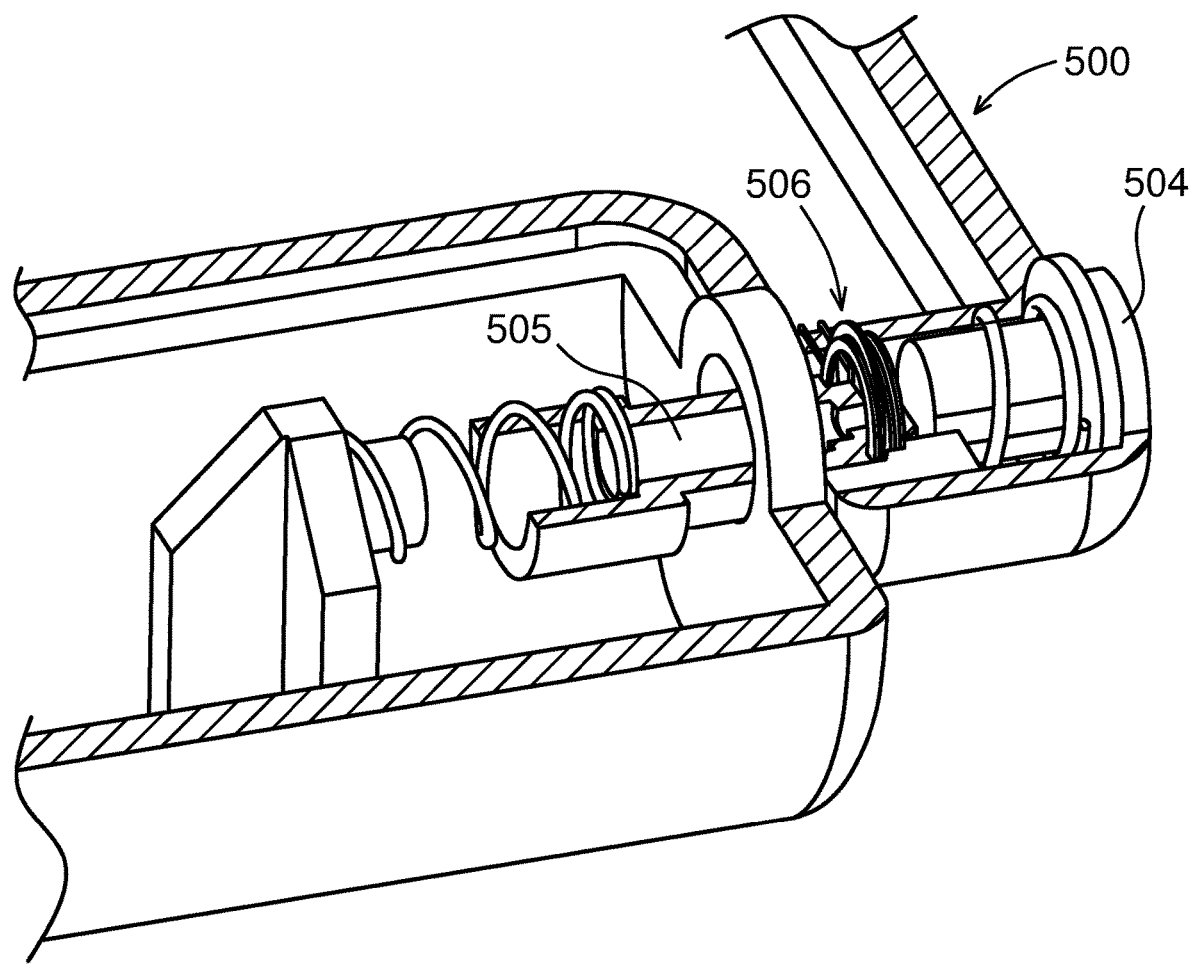
FIG. 12 is a partial perspective view of a powered quick disconnect for a toilet seat according to the present disclosure.

In accordance with the present disclosure, a design for a seat 500 that can be easily added/removed from a toilet, seat topper, seat lifter, etc. is provided. This allows for easier installation of a new seat 500 to accommodate upgraded seats and/or seat sensors. Referring to FIG. 12, a powered quick disconnect mechanism is shown. The seat 500 is removed by pressing in on the spring-loaded button 504. This moves the spring-loaded axle 505 out of the seat to allow the seat 500 to be removed. The electrical connector 506 automatically connects and disconnects with physical connection. The electrical connector 506 comprises a ring connector that maintains electrical connection throughout the seat's range of motion. This provides for electrical power and/or data connections to sensors in the seat.

In various exemplary embodiments, the sensor includes an active component (i.e., sensor or chip component in physical contact with the fluid sample) that is contacted by the fluid sample supplied by the manifold. In various exemplary embodiments, the interface between the manifold and the MFC comprises cavities at the connections to deliver and remove fluids that are shaped to mate with the surface of the MFC directly, possibly in combination with a sealing gasket or with a compliant sealing material built into the manifold directly. The sensor chip may be held in place by a mechanical fastener with sufficient uniform pressure to form a fluidic seal to the manifold.

In various exemplary embodiments, the medical toilet includes additional health and wellness sensors that may be located in a variety of location. In some embodiments, the seat may contain health and wellness sensors to measure pulse, blood pressure, blood oxygenation, electrocardiography, body temperature, body weight, excreta content, excreta weight, excreta volume, excreta temperature, excreta density, excreta flow rate, and other health and wellness indicators. In a preferred embodiment, the seat is attached to the toilet via a powered quick disconnect system that allows the seat to be interchangeable. This facilitates installing custom seats to include user-specific tests based on known health conditions. It also facilitates installing upgraded seats as sensor technology improves.

In various exemplary embodiments, the lid may contain health and wellness sensors that interact with the user's back or that analyze gases in the bowl after the lid is closed.

In various exemplary embodiments, the medical toilet includes software and hardware controls that are pre-set so that any manufacturer can configure their devices (i.e., analytical test devices) to work in the system. In a preferred embodiment, the system includes a software stack that allows for data channels to transfer data from the sensors in the medical toilet to cloud data systems. The software and hardware controls and/or software stack may be stored in the medical toilet or remotely. This would allow scientists to place sensors, reagents, etc. in the system to obtain data for their research. It also allows user data to be individually processed, analyzed, and delivered to the user, or their health care provider, digitally (e.g., on a phone, tablet, or computer application). The seat may also contain sensors to measure fluid levels in the toilet. This could include proximity sensors. Alternatively, tubes in fluid communication with the bowl water could be used to determine changes to bowl fluids (e.g., volume, temperature, rate of changes, etc.).

All patents, published patent applications, and other publications referred to herein are incorporated herein by reference. The invention has been described with reference to various specific and preferred embodiments and techniques. Nevertheless, it is understood that many variations and modifications may be made while remaining within the spirit and scope of the invention.

What is claimed is:

1. An analytical toilet comprising:
   a bowl for receiving excreta from a user;
   a base supporting the bowl; and
   one or more receptacles, each comprising:
      a connection interface for receiving an analytical test device into the receptacle, the receptacle comprising:
      a mechanical attachment to secure the analytical test device in place in the receptacle,
      a fluidic connection,
      a power supply, and
      a data connection;
   wherein the analytical test device is adapted to provide data useful to the user; and
   wherein the analytical test device is adapted to be attached into and detached out of one of the one or more receptacles.

2. The analytical toilet of claim 1 wherein at least one receptacle is adapted to provide at least one fluid inlet to and at least one fluid outlet from the analytical test device.

3. The analytical toilet of claim 1 further comprising a manifold comprising multiple flow paths and valves for providing fluids to an analytical test device in the one or more receptacles.

4. The analytical toilet of claim 3 wherein the manifold further comprises one or more mixing chambers for sample preparation.

5. The analytical toilet of claim 3 further comprising one or more fluid supplies from outside sources and internal reservoirs.

6. The analytical toilet of claim 5 further comprising at least one sensor for detecting a level of fluid in the one or more internal reservoirs.

7. The analytical toilet of claim 6 wherein the at least one sensor comprises one or more of a weight sensor, pressure sensor, or proximity sensor.

8. The analytical toilet of claim 5 wherein the plurality of fluid supplies includes at least one of excreta, buffer solutions, chemical reagents, air, biomarkers, dilution solutions, calibration solutions, fragrances, sterilizers, flushing fluid, rinsing fluid, cleansing fluids, electrolyzed water, air, and water.

9. The analytical toilet of claim 1 wherein the analytical test device measures at least one of pulse, blood pressure, blood oxygenation, electrocardiography, body temperature, body weight, excreta content, excreta weight, excreta volume, excreta temperature, excreta density, and excreta flow rate.

10. The analytical toilet of claim 1 wherein the at least one-analytical test device further comprises one or more of an MOSFET, CCD, bioFET, an electrochemical cell, spectrometry, laser excitation, ultraviolet excitation, electrophoresis, amperometry, colorimetric analysis, and chromatography.

11. The analytical toilet of claim 1 further comprising a processor adapted to receive signals from at least one of the analytical test devices in the receptacles.

12. The analytical toilet of claim 11 wherein the processor manages the data connection and the power supply for the analytical test devices needing them.

13. The analytical toilet of claim 1 further comprising a data connection from the toilet that transmits data to a health care provider.

14. The analytical toilet of claim 1 further comprising a data connection from the toilet that transmits data to a data display for the user.

15. The analytical toilet of claim 1 further comprising one or more health and wellness sensors located in a seat.

16. The analytical toilet of claim 1 further comprising one or more health and wellness sensors located in the bowl.

17. The analytical toilet of claim 1 further comprising one or more health and wellness sensors located in a lid.

18. The analytical toilet of claim 1 further comprising at least one standardized interface between the one or more receptacles and analytical test devices.

19. The analytical toilet of claim 3 wherein the manifold further comprises a relatively large channel for direct disposal of excreta in the bowl.

20. The analytical toilet of claim 1 wherein the analytical test device comprises a microfluidic chip.

21. The analytical toilet of claim 1 wherein the analytical test device further comprises a lab-on-chip.

* * * * *